United States Patent
Christen et al.

(10) Patent No.: US 10,413,605 B2
(45) Date of Patent: Sep. 17, 2019

(54) COMBINATION THERAPY FOR THE TREATMENT OF AUTOIMMUNE DISEASES

(71) Applicant: Fraunhofer-Gesellschaft zur Förderung der angewandten Forschung e.V., München (DE)

(72) Inventors: Urs Christen, Bad Vilbel (DE); Stanley Lasch, Darmstadt (DE); Michael Parnham, Bad Soden/Ts (DE)

(73) Assignee: FRAUNHOFER-GESELLSCHAFT ZUR FÖRDERUNG DER ANGEWANDTEN FORSCHUNG E.V., Munich (DE)

( * ) Notice: Subject to any disclaimer, the term of this patent is extended or adjusted under 35 U.S.C. 154(b) by 0 days.

(21) Appl. No.: 15/301,130

(22) PCT Filed: Apr. 8, 2014

(86) PCT No.: PCT/EP2014/057077
§ 371 (c)(1),
(2) Date: Sep. 30, 2016

(87) PCT Pub. No.: WO2015/154795
PCT Pub. Date: Oct. 15, 2015

(65) Prior Publication Data
US 2017/0021018 A1    Jan. 26, 2017

(51) Int. Cl.
| | | |
|---|---|---|
| *A61K 39/395* | (2006.01) | |
| *C07K 16/00* | (2006.01) | |
| *C07K 16/24* | (2006.01) | |
| *C07K 16/28* | (2006.01) | |
| *C12N 15/113* | (2010.01) | |
| *A61K 35/744* | (2015.01) | |
| *A61K 39/00* | (2006.01) | |
| *A61K 35/00* | (2006.01) | |

(52) U.S. Cl.
CPC ........ *A61K 39/3955* (2013.01); *A61K 35/744* (2013.01); *C07K 16/24* (2013.01); *C07K 16/2809* (2013.01); *C12N 15/113* (2013.01); *C12N 15/1138* (2013.01); *A61K 2035/115* (2013.01); *A61K 2039/505* (2013.01); *A61K 2039/507* (2013.01); *A61K 2039/545* (2013.01); *A61K 2039/55* (2013.01); *C07K 2317/76* (2013.01); *C12N 2310/14* (2013.01)

(58) Field of Classification Search
None
See application file for complete search history.

(56) References Cited

U.S. PATENT DOCUMENTS

2012/0263733 A1   10/2012   Lillard, Jr.

FOREIGN PATENT DOCUMENTS

| WO | WO 2007/009064 A2 | 1/2007 |
| WO | WO 2012/098238 A1 | 7/2012 |
| WO | WO 2014/003742 A1 | 1/2014 |

OTHER PUBLICATIONS

Takiishi et al. 2012. J. Clin. Invest. 122:1717-1725.*
Froud et al. 2005. Am. J. Transplantation. 5:2037-2046.*
Rosenblum et al. 2012. Sci Transl Med. 14:1-20.*
Cho et al. 2015. Nature Medicine. 21:730-738.*
Antonelli, A. et al., "Chemokine (C—X—C motif) ligand (CXCL)10 in autoimmune diseases." *Autoimmunity Reviews*, 2013, 13(3):272-280.
Belmar, N. et al., "Dissociation of efficacy and cytokine release mediated by an Fc-modified anti-CD3 mAb in a chronic experimental autoimmune encephalomyelitis model." *Journal of Neuroimmunology*, 2009, 212(1-2):65-73.
Daifotis, A. et al., "Anti-CD3 clinical trials in type 1 diabetes mellitus," *Clinical Immunology*, 2013, 149(3):268-278.
Fife, B. et al., "CXCL10 (INF-gamma-inducible protein-10) control of encephalitogenic CD4+ T cell accumulation in the central nervous system during experimental autoimmune encephalomyelitis." *The Journal of Immunology*, Jun. 2001, 166:7617-7624.
Hu, C. et al., "Combination Treatment With Anti-CD20 and Oral Anti-CD3 Prevents and Reverses Autoimmune Diabetes." *Diabetes*, Feb. 2013, 62(8): 2849-2858.
Morimoto, J. et al., "CXC chemokine ligand 10 neutralization suppresses the occurrence of diabetes in nonobese diabetic mice through enhanced beta cell proliferation without affecting insulitis." *The Journal of Immunology*, Dec. 2004, 173(11):7017-7024.
Perl, S. et al., "Addition of Rapamycin to Anti-CD3 Antibody Improves Long-Term Glycaemia Control in Diabetic NOD Mice." *PLOS ONE*, Jun. 2013, 8(6): e67189.
Shah, P. et al., "CXCL10 antagonism improves insulin sensitivity, inflammation, beta cell function, survival and mass." *EADS*, Oct. 2012, Abstract.
Shigihara, T. et al., "CXCL10 DNA Vaccination Prevents Spontaneous Diabetes through Enhanced Cell Proliferation in NOD Mice," *The Journal of Immunology*, Dec. 2005, 175(12): 8401-8408.
Tooley, J. et al., "New and future immunomodulatory therapy in type 1 diabetes," *Trends in Molecular Medicine*, Mar. 2012, 18(3): 173-181.
Chen, Yu, et al., "Effective Reversal of New-Onset Type 1 Diabetes by Treatment with Low Dose Anti-CD3 Monoclonal Antibodies." Chinese Journal of Comparative Medicine, Apr. 2008, 18(4): 47-51.

* cited by examiner

*Primary Examiner* — Shulamith H Shafer
(74) *Attorney, Agent, or Firm* — Saliwanchik, Lloyd & Eisenschenk

(57) ABSTRACT

The present invention pertains to compounds and their combination for use in the prevention or therapy of a subject suffering from an autoimmune disease such as diabetes type 1. Provided are antagonists of T-cells that are used in combination with antagonists of the cytokine CXCL10, sequentially or concomitantly, in a subject suffering from an autoimmune disease, in particular diabetes type 1.

10 Claims, 3 Drawing Sheets

COMBINATION THERAPY FOR THE TREATMENT OF AUTOIMMUNE DISEASES

CROSS REFERENCE TO A RELATED APPLICATION

Figure 1:
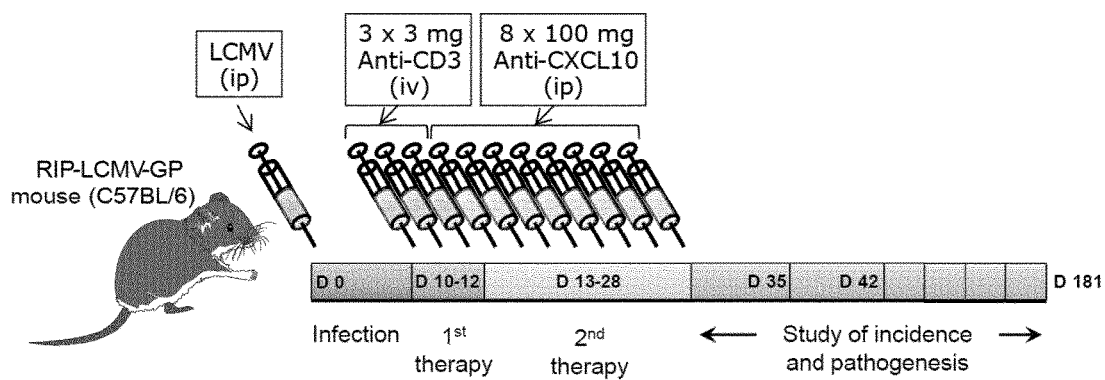

This application is a National Stage Application of International Application Number PCT/EP2014/057077, filed Apr. 8, 2014; which is incorporated herein by reference in its entirety.

FIELD OF THE INVENTION

The present invention pertains to compounds and their combination for use in the prevention or therapy of a subject suffering from an autoimmune disease such as diabetes type 1. Provided are antagonists of T-cells that are used in combination with antagonists of the cytokine CXCL10, sequentially or concomitantly, in a subject suffering from an autoimmune disease, in particular diabetes type 1.

DESCRIPTION

Diabetes type 1 is a serious autoimmune disorder resulting in the destruction of insulin producing beta cells of the Langerhans islets in the pancreas by the immune system. Without the constant supplementation of insulin, patients suffering from type 1 diabetes will as a result of the destruction of beta cells, develop hyperglycemia, which is a condition characterized by an excessive amount of glucose circulating in the blood plasma. In absence of insulin-supplementation patients will eventually die from the toxic blood glucose levels. Destruction progresses subclinically over months or years until beta-cell mass decreases to the point that insulin concentrations are no longer adequate to control plasma glucose levels. The type 1 diabetes generally develops in childhood or adolescence and until recently was the most common form diagnosed before age 30; however, it can also develop in adults. Even under constant insulin supplementation, treated patients develop long term damages such as severe disorders of the blood circulation and blindness.

Before the immune system of a patient starts destroying beta cells, the administration of immune-suppressants is believed to prevent or at least delay the progression of the disease. Examples include the administration of Cyclosporine A, an immunosuppressive agent, that has apparently halted destruction of beta cells, but its nephrotoxicity and other side effects make it highly inappropriate for long-term use.

CD3 is expressed on T cells. It has been recently demonstrated in humans that short term treatment of new onset Type 1 diabetic patients with an antibody against CD3 is able to attenuate the further destruction of beta-cells, thereby facilitating improved glycemic control of the patients. Ultimately, this gives the patients a better prognosis with respect to the development of diabetic late complications. Anti-CD3 antibodies, including teplizumab and otelixizumab, might preserve insulin production (as evidenced by sustained C-peptide production) in newly diagnosed type 1 diabetes patients. However, in 2011, Phase III studies with otelixizumab and teplizumab both failed to show clinical efficacy, potentially due to an insufficient dosing schedule. Generally, the administration of CD3 antibodies might only delay disease progression but not prevent beta cell destruction on the long term (Keymeulen B et al., *N Engl J Med* 2005). An anti-CD20 antibody, rituximab, inhibits B cells and has been shown to provoke C-peptide responses three months after diagnosis of type 1 diabetes, but long-term effects of this have also not been reported.

Currently, there are several therapies available to manage blood glucose levels as a treatment for diabetes type I, like regular insulin injections or automated insulin pumps. Such therapies are experienced as unpleasant by the patients and interfere with everyday life. An alternative treatment of diabetes type 1 is the infusion of allogeneic islets of Langerhans isolated from cadaveric donor pancreata into the portal vein. This method is known as the Edmonton Protocol. Disadvantage of this method is that it is rather inefficient in that approximately 80% of the transplanted islets die within a few days after infusion. Furthermore, insulin independence is usually not sustainable in the long term, with typically less than half of the treated patients being insulin independent one year after the treatment. Another disadvantage of the Edmonton Protocol is that multiple, preferably three, donor pancreata are needed for the treatment of one patient. This contributes to the already existing lack organ donors.

Hence, until this day there is no therapy for diabetes type 1 available that provides a long-term control of the disease. Although many treatment combinations may be theoretically thinkable, no combination treatment, in particular including immune suppressive agents, in the prior art yielded satisfactory results to date. For the skilled artisan it remains a challenge to design a therapy against the disease that could provide measurable advantages over the current treatment options. Therefore, the present invention seeks to provide a novel therapeutic approach to treat autoimmune diseases such as diabetes type 1.

The above problem is solved in a first aspect by a T-cell-antagonist for use in the prevention or treatment of an autoimmune disease in a subject, wherein said subject is additionally treated with a C-X-C motif chemokine 10 (CXCL10)-antagonist.

C-X-C motif chemokine 10 (CXCL 10) is a chemokine binding to the receptor CXCR3 and that directs migration of CXCR3-bearing cells, including natural killer (NK) cells and activated T cells. One role of NK cells and T cells in general is to facilitate the clearance of viruses, either by direct lysis of virally-infected cells or inhibition of viral replication through the release of soluble mediators such as IFN-γ. CXCL10 is also known as Interferon gamma inducible protein 10 (IP-10). The denominations CXCL10 and IP-10 denote the same protein.

The present invention now provides a combination therapy aiming at the depletion or inhibition of T-cells in a subject suffering from diabetes type 1, for example via administration of an anti-CD3 antibody, in combination with the administration of an antagonist of the cytokine CXCL10. Surprisingly, the combination therapy of the invention proved to be much more effective than either treatment alone over a long period of time. Hence, the combinatorial approach of using a T-cell-antagonist with a CXCL10-antagonist provides a new strategy for preventing the destruction of beta cells by a subject's own immune system. Specific advantages of the combination of the invention comprise the synergistic activity of both compounds of the invention compared to their single use, and therefore a better treatment and long term suppression of diabetes type 1, as supported by the disclosed examples.

In one preferred embodiment said prevention or treatment in accordance with the invention comprises the administration of said T-cell-antagonist to a subject suffering from an autoimmune disease, and wherein said subject received, receives or will receive a treatment with a CXCL 10-antagonist.

Therefore, the present embodiment relates to the treatment of a specific group of subjects suffering from an autoimmune disease, wherein the subjects are undergoing or indicated for a treatment with a CXCL10-antagonist. The CXCL10-antagonist treatment may be performed during the same period of time as the T-cell-antagonist treatment, or alternatively is done before or after. The latter can be preferable in order to avoid stacking of adverse effects. The person of skill understands that the inventive result is achieved when the physiological effects of a T-cell-antagonist of the invention and a CXCL10-antagonist of the invention overlap, or are combined in a subject in need of such a treatment. It is not particularly necessary to administer the combination as a mixture of both agents. Since after a last dose of a medicament is administered in a certain therapy, usually the physiological effects induced by the medicament will not diminish immediately, but prolong after administration and slowly decrease over time. Therefore, using the antagonists of the invention in sequential therapeutic cycles instead at the same time, the medical practitioner still can achieve a combination of the clinical effects of both antagonists. Thus sequential administration regimes are falling under the meaning of a combination therapy in accordance with the present invention.

Therefore, in one preferred embodiment of the invention the said prevention or treatment of the invention comprises the concomitant or sequential administration of said T-cell-antagonist and said CXCL10-antagonist.

In another aspect of the invention the problem is solved by a C-X-C motif chemokine 10 (CXCL10)-antagonist for use in the prevention or treatment of an autoimmune disease in a subject, wherein said subject is additionally treated with a T-cell-antagonist. In this aspect one preferred embodiment relates to a use in prevention or treatment which comprises the administration of said CXCL10-antagonist to a subject suffering from an autoimmune disease, and wherein said subject received, receives or will receive a treatment with a T-cell-antagonist. The above said for the T-Cell-antagonists of the invention apply correspondingly to the CXCL10-antagonist of the invention.

Hence, also in this aspect one preferred embodiment of the invention pertains the CXCL10-antagonist, wherein said prevention or treatment comprises the concomitant or sequential administration of said CXCL10-antagonist and said T-cell-antagonist.

A third aspect of the invention then pertains to a combination comprising (i) a T-cell-antagonist and (ii) a C-X-C motif chemokine 10 (CXCL10)-antagonist for concomitant or sequential use in the prevention or treatment of an autoimmune disease.

The term "combination" means in this context a combination of the two active substances (antagonists) in a formulation or as a combination in the sense of individual formulations of the active substances administered at specified intervals from one another in a therapeutic treatment. Thus the term "combination" shall include the clinical reality of a co-administration of two antagonists, as it is described in context of the present invention.

Co-administration: In the context of the present application, co-administration of two compounds is defined as administration of the two compounds to the patient within one year, including separate administration of two medicaments each containing one of the compounds as well as simultaneous administration whether or not the two compounds are combined in one formulation or whether they are in two separate formulations.

Embodiments of the invention that are preferred relate to the above combination for use, wherein antagonists (i) and (ii) are combined by sequential or concomitant administration to a subject during said prevention or treatment, preferably wherein the antagonists are sequentially administered during said prevention or treatment.

In some embodiments it is preferred that first the T-cell-antagonist is administered to said subject, and subsequently the CXCL10-antagonist is administered.

The antagonists of the present invention are preferably selected from the group of compounds consisting of inhibitory RNA, inhibitory antibody, and/or small molecule. Detailed descriptions of the antagonists of the invention are provided herein below, and shall define the antagonist of the invention in all of the various described aspects and embodiments.

In the context of the present invention the term "autoimmune disease" is preferably diabetes, and even more preferably type 1 diabetes. Thus all aspects and embodiments of the invention as described herein refer in even more preferred embodiments to the type 1 diabetes. The terms "type 1 diabetes" and "diabetes type 1" refer to the same disease In certain preferred embodiments the T-cell-antagonist for use according to any one of the aspects of the invention is an antibody against CD3. The CXCL10-antagonist for use in according with any one of the aspects of the invention is preferably selected from the group consisting of an anti-CXCL10 antibody, soluble C-X Chemokine receptor 3 (CXCR3), and a CXCR3-fusion protein.

Further preferred embodiments of the invention in all its aspects pertain to the additional use of at least one alternative therapeutic that is effective against said autoimmune disease. Preferably said additional therapeutic is administered to said subject. For example said at least one additional therapeutic is selected from the group of islet cell-antigen, rapamycin and a probiotic, such as *Lactococcus lactis*. More examples of additional therapeutics to be used in all the aspects and embodiments of the invention are described herein below.

The problem of the invention is further solved by a method for the prevention or treatment of an autoimmune disease in a subject, the method comprising the steps of administering to said subject a therapeutically effective amount of a T-cell-antagonist and a CXCL 10-antagonist. In a preferred embodiment of this aspect of the invention said T-cell-antagonist and said CXCL10-antagonist are administered to said subject sequentially, or concomitantly. Most preferred is a sequential administration wherein first a T-cell-antagonist of the invention is administered followed by the administration of a CXCL10-antagonist.

Said autoimmune disease is preferably diabetes, most preferably diabetes type 1.

In some embodiments the method of the invention may comprise that at least one additional therapeutic effective against said autoimmune disease is administered to said patient. Such an additional therapeutic is selected from the group of islet-cell-antigen, rapamycin and a probiotic, such as *Lactococcus lactis*. Other additional therapeutics that are preferably used in context of this embodiment are disclosed herein below.

In accordance with the present invention a "subject" is a mammal, preferably a human, or a human patient suffering from an autoimmune disease such as diabetes type 1. More preferably in context of the invention said subject is suffering from type 1 diabetes and said subject already received a pancreas and/or islet transplantation.

T-cell-antagonists

A T-cell-antagonist in context with the invention is particularly a compound that reduces the number or activity of T-cells. This can be achieved for example by the use of an inhibitory antibody directed against CD3 which is an important component of the T-cell receptor assembly. The T-cell receptor mediates the immune recognition of the T-cells via binding to the target antigen. Anti-CD3 antibodies bind to, and inactivate CD3, and therefore inactivate the respective T-cell. However, the central idea of the present invention pertains to a combinatorial treatment comprising (i) the inhibition of T-cells in combination with (ii) antagonizing the activity of the cytokine CXCL10. Therefore, the term "T-cell-antagonist" in accordance with the invention refers to generally all means that can supress the immune function or expression of T-cells. For example, alternative agents to CD3-antagonists are antagonists of CD4 or CD8, which can be used to inactivate T-cells in a subject. A combination of CD4 and CD8-antagonists may be for example preferably used in context of the present invention.

CD3 (cluster of differentiation 3) T-cell co-receptor is a protein complex and is composed of four distinct chains. In mammals, the complex contains a CD3γ chain, a CD3δ chain, and two CD3ε chains. These chains associate with a molecule known as the T-cell receptor (TCR) and the ζ-chain to generate activation signal in T lymphocytes. The TCR, ζ-chain, and CD3 molecules together comprise the TCR complex.

Specifically preferred in all embodiments of the invention is therfore the use of a CD3-antagonist as a T-cell-antagonist. As used herein, the term "CD3-antagonist" means a substance that affects a decrease in the amount or rate of CD3 expression or activity, and thereby T-cell function. Such a substance can act directly, for example, by binding to CD3 and decreasing the amount or rate of CD3 expression or activity. A CD3-antagonist can also decrease the amount or rate of CD3 expression or activity, for example, by binding to CD3 in such a way as to reduce or prevent interaction of CD3 with other components of the T-cell receptor complex; by binding to CD3 and modifying it, such as by removal or addition of a moiety; and by binding to CD3 and reducing its stability. A CD3-antagonist can also act indirectly, for example, by binding to a regulatory molecule or gene region so as to modulate regulatory protein or gene region function and affect a decrease in the amount or rate of CD3 expression or activity. Thus, a CD3-antagonist can act by any mechanisms that result in decrease in the amount or rate of CD3 expression or activity.

A CD3-antagonist can be, for example, a naturally or non-naturally occurring macromolecule, such as a polypeptide, peptide, peptidomimetic, nucleic acid, carbohydrate or lipid. A CD3-antagonist further can be an antibody, or antigen-binding fragment thereof, such as a mono-clonal antibody, humanized antibody, chimeric antibody, minibody, bifunctional antibody, single chain antibody (scFv), variable region fragment (Fv or Fd), Fab or F(ab)2. A CD3-antagonist can also be polyclonal antibodies specific for CD3. A CD3-antagonist further can be a partially or completely synthetic derivative, analog or mimetic of a naturally occurring macromolecule, or a small organic or inorganic molecule.

A CD3-antagonist that is an antibody can be, for example, an antibody that binds to CD3 and inhibits formation of the T-cell receptor complex, or alters the activity of a molecule that regulates CD3 expression or activity, such that the amount or rate of CD3 expression or activity is decreased. An antibody useful in a method of the invention can be a naturally occurring antibody, including a monoclonal or polyclonal antibodies or fragment thereof, or a non-naturally occurring antibody, including but not limited to a single chain antibody, chimeric antibody, bifunctional antibody, complementarity determining region-grafted (CDR-grafted) antibody and humanized antibody or an antigen-binding fragment thereof.

A CD3-antagonist that is a nucleic acid can be, for example, an anti-sense nucleotide sequence, an RNA molecule, or an aptamer sequence. An anti-sense nucleotide sequence can bind to a nucleotide sequence within a cell and modulate the level of expression of CD3, CXCL0 receptor or modulate expression of another gene that controls the expression or activity of CD3. Similarly, an RNA molecule, such as a catalytic ribozyme, can bind to and alter the expression of the CD3 gene, or other gene that controls the expression or activity of CD3. An aptamer is a nucleic acid sequence that has a three dimensional structure capable of binding to a molecular target.

A CD3-antagonist that is a nucleic acid also can be a double-stranded RNA molecule for use in RNA interference methods. RNA interference (RNAi) is a process of sequence-specific gene silencing by post-transcriptional RNA degradation, which is initiated by double-stranded RNA (dsRNA) homologous in sequence to the silenced gene. A suitable double-stranded RNA (dsRNA) for RNAi contains sense and antisense strands of about 21 contiguous nucleotides corresponding to the gene to be targeted that form 19 RNA base pairs, leaving overhangs of two nucleotides at each 3' end (Elbashir et al., Nature 411:494-498 (2001); Bass, Nature 411:428-429 (2001); Zamore, Nat. Struct. Biol. 8:746-750 (2001)). dsRNAs of about 25-30 nucleotides have also been used successfully for RNAi (Karabinos et al., Proc. Natl. Acad. Sci. USA 98:7863-7868 (2001). dsRNA can be synthesized in vitro and introduced into a cell by methods known in the art.

Specifically preferred embodiments of the invention pertain to the anti-CD3 antibodies known as teplizumab and/or otelixizumab.

CXCL10-antagonist

As used herein, the term "CXCL10-antagonist" means a substance that affects a decrease in the amount or rate of CXCL10 expression or activity. Such a substance can act directly, for example, by binding to CXCL10 and decreasing the amount or rate of CXCL10 expression or activity. A CXCL10-antagonist can also decrease the amount or rate of CXCL10 expression or activity, for example, by binding to CXCL 10 in such a way as to reduce or prevent interaction of CXCL10 with a CXCL10 receptor; by binding to CXCL10 and modifying it, such as by removal or addition of a moiety; and by binding to CXCL10 and reducing its stability. A CXCL10-antagonist can also act indirectly, for example, by binding to a regulatory molecule or gene region so as to modulate regulatory protein or gene region function and affect a decrease in the amount or rate of CXCL10 expression or activity. Thus, a CXCL10-antagonist can act by any mechanisms that result in decrease in the amount or rate of CXCL10 expression or activity.

A CXCL10-antagonist can be, for example, a naturally or non-naturally occurring macromolecule, such as a polypeptide, peptide, peptidomimetic, nucleic acid, carbohydrate or lipid. A CXCL10-antagonist further can be an antibody, or antigen-binding fragment thereof, such as a monoclonal antibody, humanized antibody, chimeric antibody, minibody, bifunctional anti-body, single chain antibody (scFv), variable region fragment (Fv or Fd), Fab or F(ab)2. A CXCL10-antagonist can also be polyclonal antibodies specific for CXCL10. A CXCL10-antagonist further can be a partially or completely synthetic derivative, analog or mimetic of a naturally occurring macromolecule, or a small organic or inorganic molecule.

A CXCL10-antagonist that is an antibody can be, for example, an antibody that binds to CXCL10 and inhibits binding to a CXCL10 receptor, or alters the activity of a molecule that regulates CXCL10 expression or activity, such that the amount or rate of CXCL10 expression or activity is decreased. An antibody useful in a method of the invention can be a naturally occurring antibody, including a monoclonal or polyclonal antibodies or fragment thereof, or a non-naturally occurring antibody, including but not limited to a single chain antibody, chimeric antibody, bifunctional antibody, complementarity determining region-grafted (CDR-grafted) antibody and humanized antibody or an antigen-binding fragment thereof.

A CXCL10-antagonist that is a nucleic acid can be, for example, an anti-sense nucleotide sequence, an RNA molecule, or an aptamer sequence. An anti-sense nucleotide sequence can bind to a nucleotide sequence within a cell and modulate the level of expression of CXCL10, CXCL0 receptor or modulate expression of another gene that controls the expression or activity of CXCL10. Similarly, an RNA molecule, such as a catalytic ribozyme, can bind to and alter the expression of the CXCL10 gene, or other gene that controls the expression or activity of CXCL10. An aptamer is a nucleic acid sequence that has a three dimensional structure capable of binding to a molecular target.

A CXCL10-antagonist that is a nucleic acid also can be a double-stranded RNA molecule for use in RNA interference methods. RNA interference (RNAi) is a process of sequence-specific gene silencing by post-transcriptional RNA degradation, which is initiated by double-stranded RNA (dsRNA) homologous in sequence to the silenced gene. A suitable double-stranded RNA (dsRNA) for RNAi contains sense and antisense strands of about 21 contiguous nucleotides corresponding to the gene to be targeted that form 19 RNA base pairs, leaving overhangs of two nucleotides at each 3' end (Elbashir et al., Nature 411:494-498 (2001); Bass, Nature 411:428-429 (2001); Zamore, Nat. Struct. Biol. 8:746-750 (2001)). dsRNAs of about 25-30 nucleotides have also been used successfully for RNAi (Karabinos et al., Proc. Natl. Acad. Sci. USA 98:7863-7868 (2001). dsRNA can be synthesized in vitro and introduced into a cell by methods known in the art.

In preferred embodiments the CXCL10-antagonist of the invention is the antibody MDX-1100, or a functional derivative or fragment thereof. MDX-1100 is a fully human anti-IP-10 (anti-CXCL10) monoclonal antibody (produced by Medarex, since acquired by Bristol-Myers Squibb) that binds to IP-10 with high affinity but not to other CXCR3 ligands, CXCL9, or CXCL11.

Additional Therapeutics

The combined treatment in accordance with the invention may further include additional pharmacologically active substances (therapeutics), e.g. selected from antidiabetic agents, antiobesity agents, appetite regulating agents, antihypertensive agents, agents for the treatment and/or prevention of complications resulting from or associated with diabetes and agents for the treatment and/or prevention of complications and disorders resulting from or associated with obesity. Most importantly, when the treatment is used in already diagnosed Type 1 or LADA diabetic patients, co-therapy with insulin, insulin analogues or oral antidiabetic agents will be common. Examples of these pharmacologically active substances are : Insulin, GLP-1 agonists, sulphonylureas, biguanides, meglitinides, glucosidase inhibitors, glucagon antagonists, DPP-IV (dipeptidyl peptidase-IV) inhibitors, inhibitors of hepatic enzymes involved in stimulation of gluconeogenesis and/or glycogenolysis, glucose uptake modulators, compounds modifying the lipid metabolism such as antihyperlipidemic agents as HMG CoA inhibitors (statins), compounds lowering food intake, RXR agonists and agents acting on the ATP-dependent potassium channel of the β-cell; Cholestyramine, colestipol, clofibrate, gemfibrozil, lovastatin, pravastatin, simvastatin, probucol, dextrothyroxine; β-blockers such as alprenolol, atenolol, timolol, pindolol, propranolol and metoprolol, ACE (angiotensin converting enzyme) inhibitors such as benazeprit, captopril, enalapril, fosinopril, lisinopril, quinapril and ramipril, calcium channel blockers such as nifedipine, felodipine, nicardipine, isradipine, nimodipine, diltiazem and verapamil, and α-blockers such as doxazosin, urapidil, prazosin and terazosin; CART (cocaine amphetamine regulated transcript) agonists, NPY (neuropeptide Y) antagonists, MC4 (melanocortin 4) agonists, orexin antagonists, TNF (tumor necrosis factor) agonists, CRF (corticotropin releasing factor) agonists, CRF BP (corticotropin releasing factor binding protein) antagonists, urocortin agonists, β3 agonists, MSH (melanocyte-stimulating hormone) agonists, MCH (melanocyte-concentrating hormone) antagonists, CCK (cholecystokinin) agonists, serotonin re-uptake inhibitors, serotonin and noradrenaline reuptake inhibitors, mixed serotonin and noradrenergic compounds, 5HT (serotonin) agonists, bombesin agonists, galanin antagonists, growth hormone, growth hormone releasing compounds, TRH (thyreotropin releasing hormone) agonists, UCP 2 or 3 (uncoupling protein 2 or 3) modulators, leptin agonists, DA agonists (bromocriptin, doprexin), lipase/amylase inhibitors, RXR (retinoid X receptor) modulators, TR 0 agonists; histamine H3 antagonists.

Compositions and Kits for Treating or Preventing Autoimmune Diseases

Another aspect of the present application relates to compositions and kits for treating or preventing autoimmune diseases. In one embodiment, the composition comprises a T-cell-antagonist as described herein above, and a CXCL10-antagonist, wherein the antagonist are preferably selected from an antibody, antibody fragment, short interfering RNA (siRNA), aptamer, synbody, binding agent, peptide, aptamer-siRNA chimera, single stranded antisense oligonucleotide, triplex forming oligonucleotide, ribozyme, external guide sequence, agent-encoding expression vector, and a pharmaceutically acceptable carrier.

As used herein the language "pharmaceutically acceptable carrier" is intended to include any and all solvents, solubilizers, fillers, stabilizers, binders, absorbents, bases, buffering agents, lubricants, controlled release vehicles, diluents, emulsifying agents, humectants, lubricants, dispersion media, coatings, antibacterial or antifungal agents, isotonic and absorption delaying agents, and the like, compatible with pharmaceutical administration. The use of such media and agents for pharmaceutically active substances is well-known in the art. Except insofar as any conventional media or agent is incompatible with the active compound, use thereof in the compositions is contemplated. Supplementary agents can also be incorporated into the compositions. In certain embodiments, the pharmaceutically acceptable carrier comprises serum albumin.

The pharmaceutical composition of the invention is formulated to be compatible with its intended route of administration. Examples of routes of administration include parenteral, e.g., intrathecal, intra-arterial, intravenous, intradermal, subcutaneous, oral, transdermal (topical) and transmucosal administration.

Solutions or suspensions used for parenteral, intradermal, or subcutaneous application can include the following components: a sterile diluent such as water for injection, saline solution, fixed oils, polyethylene glycols, glycerine; propylene glycol or other synthetic solvents; anti-bacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the injectable composition should be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the requited particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a neuregulin) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Stertes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the pharmaceutical compositions are formulated into ointments, salves, gels, or creams as generally known in the art.

In certain embodiments, the pharmaceutical composition is formulated for sustained or controlled release of the active ingredient. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from e.g. Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art.

It is especially advantageous to formulate oral or parenteral compositions in dosage unit form for ease of administration and uniformity of dosage. Dosage unit form as used herein includes physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. The pharmaceutical compositions can be included in a container, pack, or dispenser together with instructions for administration.

The present invention will now be further described in the following examples with reference to the accompanying figures and sequences, nevertheless, without being limited thereto. For the purposes of the present invention, all references as cited herein are incorporated by reference in their entireties. In the Figures:

FIG. 1: Treatment schedule for diabetic mice

Figure 2:
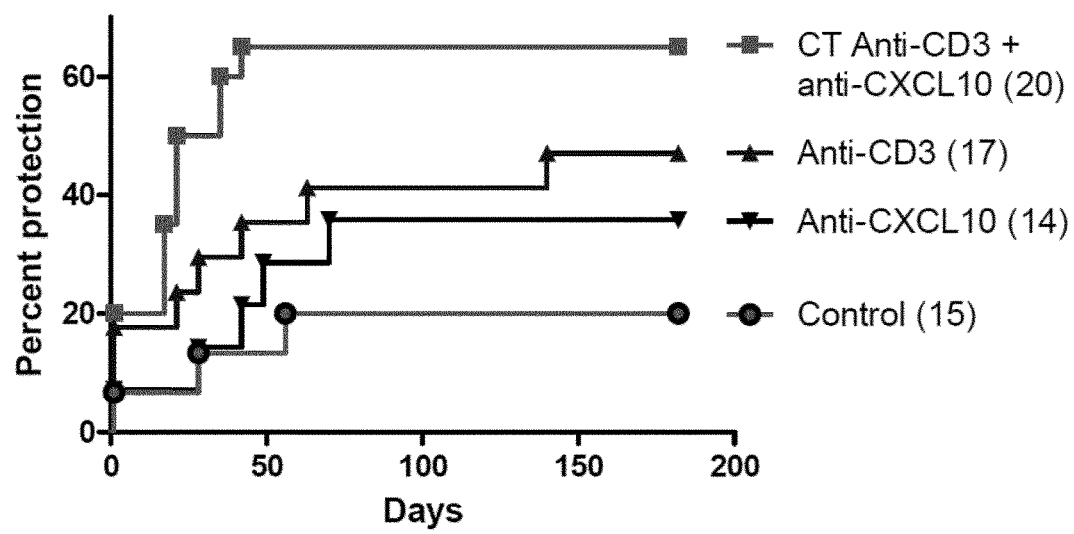

FIG. 2: Diabetes type 1 therapy: diabetic mice receiving single treatments with anti-CD3 and Anti-CXCL10 antibodies (triangles) are compared to the combination treatment (squares). Control mice that received saline solution are depicted as circles. Shown is the percent protection from diabetes.

Figure 3:
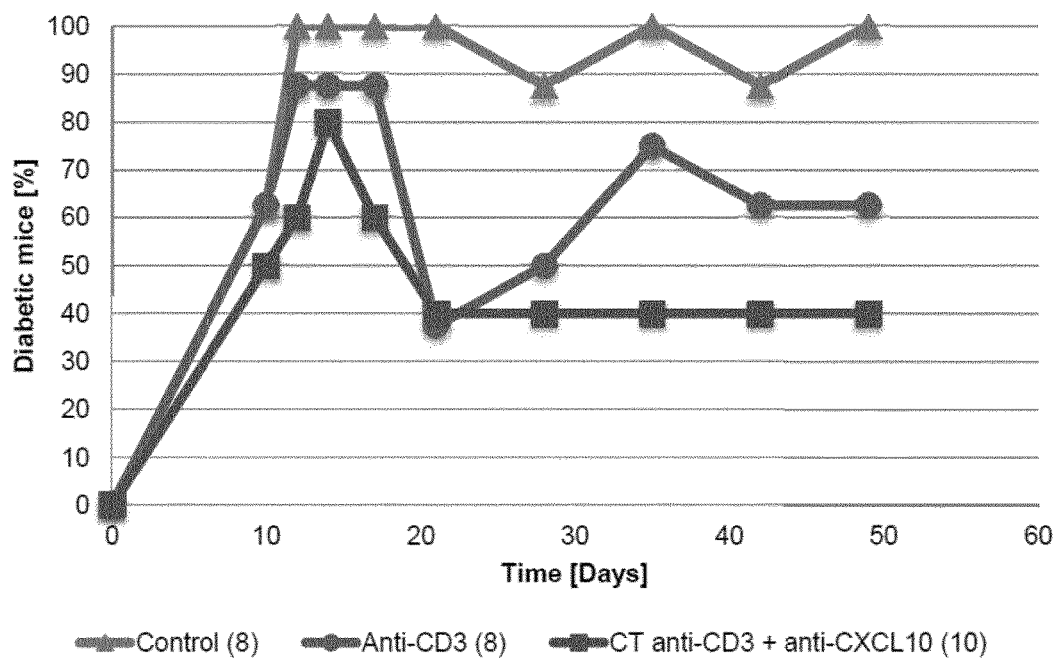

FIG. 3: Blood glucose levels: diabetic mice treated with anti-CD3 antibodies (circles) compared to the control (triangles) and the combination therapy with antibodies against CD3 and CXCL10 (squares).

EXAMPLES

Example 1

As a model for diabetes type 1 the RIP-LCMV mouse was used. Transgenic RIP-LCMV-GP mice express glycoprotein (GP) of the Lymphocytic Choriomeningitis Virus (LCMV) under the control of the rat insulin promoter (RIP). The promoter allows for the specific expression in the beta cells of the Langerhans islets of the pancreas (Oldstone MBA et al, Cell, 1991). The transgenic mice therefore express the viral GP and tolerate the protein as "self". However, infection with the LCMV induces a LCMV specific immune response that not only targets the virus but also the beta cells expressing the viral GP protein. Usually, the RIP-LCMV-GP mice develop type 1 diabetes after 10 to 14 days of the infection.

For the experiments, the above mice when diabetic were treated for three days with 3 μg/day anti-CD3 antibody (Armenian hamster anti-mouse CD3e IgG F(ab'), clone 145-2C11; Chatenoud L, et al. 1997, J Immunol.). Subsequently, the mice were treated three times a week with 100 μg anti-CXCL10 antibody (Armenian hamster anti-mouse Crg-2 IgG, clone 1F11; Khan IA et al., Immunity 2000) to a total of 10 injections (see FIG. 1). Control experiments pertain to the single treatments with the above antibodies, and treatment with saline solution.

Diabetic mice receiving single treatments with Anti-CD3 and Anti-CXCL10 antibodies show a moderate but not significant effect. Diabetic mice treated with both antibodies show a significantly enhanced therapeutic effect (FIG. 2): combination therapy vs. control (p=0.01), anti-CD3 vs. control (p=0.12). Significance was determined using the Log-rank (Mantel-Cox) Test.

Diabetic mice treated with anti-CD3 antibodies alone showed temporary reduction of blood glucose levels compared to the control. However, after a short time, the blood glucose levels in-crease above the diabetic threshold (>300 mg/dl). Combination therapy with an-ti-bodies against CD3 and CXCL10 resulted in a long-term (more than 50 days) reduction of blood glucose levels (FIG. 3).

Therefore, the results surprisingly show that the combination therapy of the invention compared to the single treatments is advantageous and will provide a true therapy option for a long term prevention and treatment of type 1 diabetes.

The invention claimed is:

1. A composition comprising (i) an inhibitory anti-CD3-antibody and (ii) an inhibitory anti-C-X-C motif chemokine 10 (CXCL10) antibody formulated for concomitant or sequential use in the treatment of type 1 diabetes.

2. A method for the treatment of type 1 diabetes in a subject, the method comprising administering to said subject a therapeutically effective amount of an inhibitory anti-CD3-antibody and an inhibitory anti-C-X-C motif chemokine 10 (CXCL10) antibody.

3. The method according to claim 2, wherein said inhibitory anti-CD3-antibody and said inhibitory anti-CXCL10 antibody are administered to said subject sequentially, or concomitantly.

4. The method according to claim 2, wherein at least one additional therapeutically effective agent against type 1 diabetes is administered to the patient.

5. The method according to claim 4, wherein said at least one additional therapeutic agent is selected from the group of islet-cell-antigen, rapamycin and probiotics.

6. The method according to claim 2, wherein the subject is a mammal.

7. The method according to claim 2, wherein said subject received a pancreas and/or islet transplantation.

8. The method according to claim 2, wherein the subject is suffering from type 1 diabetes.

9. The method according to claim 5, wherein said probiotic is *Lactococcus lactis*.

10. The method according to claim 6, wherein said mammal is a human.

* * * * *